United States Patent [19]

Leuck et al.

[11] Patent Number: 4,908,471

[45] Date of Patent: Mar. 13, 1990

[54] METHOD FOR THE PRODUCTION OF BENZENE CARBOXYLIC ACIDS AND BENZENE DICARBOXYLIC ACID ESTERS

[75] Inventors: Hans Leuck; Hans-Jörg Westermann, both of Troisdorf, Fed. Rep. of Germany

[73] Assignee: Huels Troisdorf AG, Cologne, Fed. Rep. of Germany

[21] Appl. No.: 156,257

[22] Filed: Feb. 16, 1988

[30] Foreign Application Priority Data

Feb. 14, 1987 [DE] Fed. Rep. of Germany ....... 3704720

[51] Int. Cl.$^4$ ..................... C07C 67/39; C07C 51/265
[52] U.S. Cl. .................................. 560/77; 562/414; 422/140
[58] Field of Search ........................... 560/77; 562/414

[56] References Cited

U.S. PATENT DOCUMENTS

| | | | |
|---|---|---|---|
| 4,096,340 | 6/1978 | Fujii et al. | 560/77 |
| 4,241,220 | 12/1980 | Itaya et al. | 562/414 |
| 4,329,493 | 5/1982 | Hashizume et al. | 562/414 |
| 4,342,876 | 8/1982 | Klingman | 560/77 |
| 4,346,230 | 8/1982 | Hoffmann et al. | 560/99 |

OTHER PUBLICATIONS

Ullmann, vol. 3, (1973), pp. 388–389.

*Primary Examiner*—Werren B. Lone
*Assistant Examiner*—Vera C. Clarke
*Attorney, Agent, or Firm*—Felfe & Lynch

[57] ABSTRACT

Disclosed is a method for the production of benzene carboxylic acids and benzene carboxylic acid esters or their mixtures, while p-toloylic acid is made from p-xylene and terephthalic acid monomethyl ester is simultaneously prepared from p-toluylic acid ester. The oxidation is performed by the addition of oxidator liquid and gases containing oxygen in single orifice mixing nozzles with the formation of a highly disperse reaction phase and the single orifice mixing nozzles open into the oxidator liquid.

14 Claims, 2 Drawing Sheets

METHOD FOR THE PRODUCTION OF BENZENE CARBOXYLIC ACIDS AND BENZENE DICARBOXYLIC ACID ESTERS

BACKGROUND OF THE INVENTION

The invention is in an improved method and apparatus for the production of benzenecarboxylic acids and benzenedicarboxylic acid esters or mixture thereof by the oxidation of xylenes or toluylic acid esters by means of oxygen or gases containing oxygen, in the presence of catalysts containing heavy metal, at elevated temperatures and elevated pressure.

Terephthalic acid dimethyl esters can be prepared by oxidizing p-xylene (PX) with air in the liquid phase. In a first phase of the preparation, a methyl group of the PX is oxidized in the presence of a heavy metal catalyst to form p-toluylic acid. The acid is then esterified with methanol to p-toluylic acid methyl ester (PT-ester=PTE). PTE is then further oxidized together with PX to the terephthalic acid monomethyl ester, and is then transformed with methanol to terephthalic acid dimethyl ester end product which is separated off by distillation, while the remaining part is the so called working ester.

The two oxidation processes are performed together, insofar as possible. The liquid reaction phase placed in the reactor is a mixture preferably prepared from fresh PX and the working ester (derived from the esterification with a high content of PTE plus an amount of by-products) the amount of the working ester being the predominate portion. This reaction phase used as starting mixture allows operation in the fluid state for all of the substances to be manipulated during the production process.

The progress of the oxidation of the starting mixture to form the oxidator liquid which contains specified contents of the target products is determined by measuring the acid number of the reaction phase in the reactor which is called the "oxidator". The acid number is measured in milligrams of potassium hydroxide per gram of the oxidator liquid. By the acid number only the carboxylic acid group-COOH is measured. The selectivity of the oxidation is determined by analyzing the reactor exhaust gas in which a content of carbon monoxide and carbon dioxide indicates an undesired decarboxylation and the content of residual oxygen indicates the utilization grade of the oxygen.

Production on a large technical scale is performed continuously in the conventional process with a pressure between 0.5 and 1.1 MPa at a temperature of from 135° to 170° C. An effort is made to operate with a high air input or high yields per unit time and capacity, at a high oxygen reaction and a low yield of carbon monoxide and carbon dioxide and by-product formation, and at the same time to carry off the considerable reaction heat in a narrow temperature range in the oxidation zone adapted to the progress of the reaction. The oxidators are constructed, for example, in the form of bubble column reactors of 10 or more meters in height. The reaction gas is introduced through gas distributors in the vertical liquid column.

Limitations are created by frothing and oxygen gas breakthroughs which lower operating safety and economy. The reaction heat is carried away and recovered by evaporating boiler feed water in heat exchanging systems inside or outside of the oxidator. Highly developed but very expensive tubular reactors are standard equipment.

In another procedure the oxidation gas is introduced into the oxidator liquid by gas jets, so as to achieve high substance transformations, the reaction heat being removed as described above. In this procedure too, the amount of air introduced also is limited by elevated oxygen contents and combustion products in the exhaust gas, as well as unavoidable frothing in the oxidator. Very high or very long oxidators are required.

Due to the highly exothermic oxidation reaction, local temperature peaks are unavoidable in either process. This results in an elevated formation of CO, $CO_2$, increased amounts of low aliphatic acids and oxidation products of high molecular weight, all of which result in yield losses.

The objective therefore was to increase the selectivity and yield of the reaction, i.e., the formation of terephthalic acid monomethyl esters from PTE and of p-toluylic acid from PX as well as to increase the rate of oxidation, and by reducing the residence time of the liquid products in the oxidator to reduce the thermal stress on the products, and to manage i.e. control the increased amount of heat per unit time resulting therefrom, while maintaining favorable reaction temperatures and conditions.

SUMMARY OF THE INVENTION

The above objective and others are accomplished by the method and apparatus of the invention.

According to the invention benzene carboxylic acid or benzene dicarboxylic acid esters and their mixtures are produced by oxidizing xylenes and/or toluylic acid esters with oxygen or oxygen containing gases, in the presence of oxidation catalysts containing heavy metal, at temperatures of from 110° to 200° C., preferably 130° to 170° C., with the use of elevated pressure of 0.2 to 1.5, preferably 0.5 to 0.9 MPa absolute pressure. The catalyst-containing oxidator liquid is circulated and, with the addition of oxygen or oxygen-containing gases, it is reacted as a highly disperse reaction phase in the form of a spray through one or more single orifice mixing nozzles and returned into the reactor. Single orifice mixing nozzles are nozzles for the inside mixing of oxidation gas and reaction phase (oxidator liquid) having inside a mixing space for oxygen containing gas and the reaction phase, hereinafter referred to as nozzles throughout the specification.

By performing the reaction of the starting substances in the formed liquid reaction phase of the oxidator liquid by adding gases containing oxygen in single orifice mixing nozzles, after a highly disperse phase, which becomes the reaction phase, has been produced from the oxidation gas and the oxidator liquid, the above-described disadvantages of the known methods are greatly reduced. For example by such processing one can better manage the removal of heat at a high air input and high oxygen transformations and high yields per unit capacity and time, and lower the combustion losses and formation of undesired by-products.

Surprisingly it has been found that a very complete reaction of the oxygen takes place inside of the single orifice mixing nozzles or directly in the oxidator liquid behind them. The actual reaction takes place in a very small volume within the mixing space of the nozzle. Within a finite, but short, distance from the single orifice mixing nozzle oxygen is found nearly completely consumed. This corresponds to the analysis found in the separated exhaust gas. The amount of oxygen-containing gas which is reactable is substantially increased, i.e., at least fourfold in comparison to known methods. It is therefore possible by the invention to substantially increase the reaction speed and with it the yield per unit of capacity and time over that obtainable with the above known methods. The oxidator volume or the height of the oxidator can be considerably reduced with a simultaneous increase in the substance transformation, an increase in the selectivity, and a reduction of the formation of by-products. Surprisingly, temperature control of the highly exothermic reaction is easier to manage and substantially greater amounts of heat can be removed per unit time. The reaction chamber is small and essentially consists of only one or more also small single orifice mixing nozzles. The oxidator serves substantially only as a pump tank and as a chamber for separating the exhaust gases.

According to the invention, the fluid-bed nozzles discharge into the oxidator liquid inside of the oxidator. However, only about 0.3 to 0.5 meters level of oxidator liquid above the orifice of the single orifice mixing nozzles is necessary. Nevertheless, oxygen breakthroughs are completely prevented.

The temperature of the narrowly defined reaction zone can be set at precise levels by cooling the oxidator liquid before it enters the single orifice mixing nozzles. This can be accomplished by removing oxidator liquid from the oxidator by a pump and passing the removed liquid through a heat exchanger in the circuit or connected parallel thereto. Furthermore, the circulating liquid can be cooled by admixing an inert liquid which evaporates at the reaction temperature, preferably water or low-boiling organic liquids. The inert liquid is best injected into the single orifice mixing nozzles.

Preferably the volumetric ratio of gas to liquid, under standard conditions, is 1 to 20 parts gas to one part liquid, very preferably 3 to 8 parts to one part liquid. The nozzle feed pressure of the oxidator liquid coming from the pump is higher than the pressure in the oxidator; the nozzle feed pressure is preferably 0.1 to 3.0 MPa higher, very preferably 0.2 to 1.0 MPa, higher than the pressure in the oxidator. The pressure in the oxidator is 0.2 to 1.5 MPa absolute.

The nozzle feed pressure can be lowered or raised above the pressure of the oxidator as the oxidation progresses, i.e., as the acid number increases. In a like manner the rate of flow of the oxygen-containing gas to the rate of flow of the oxidator liquid that is recirculated and fed to the single orifice mixing nozzles can be regulated.

The temperature in the oxidator can be varied, preferably increased, according to the progress of the reaction.

It has been found desirable to maintain a mass velocity (of the mixture of gas and liquid) of 1,500 to 6,000 kg/sec m$^2$ which is effected by the pump pressure and the pressure of the air added, in the nozzles at the point of mixture of gas and fluid, i.e., at the narrowest cross section of the two-phase flow. A mass velocity of 2,000 to 4,000 kg/sec m$^2$ is preferred.

Under the above-described conditions, potential velocities (U) of the liquid of 15 to 45 m/sec, preferably 20 to 35 m/sec, are provided in the single orifice mixing nozzles for the achievement of an advantageous degree of atomization of the liquid phase. The term, potential velocity, is to be understood to mean the square root of twice the pressure difference between the nozzle feed pressure of the liquid and the oxidator pressure, divided by the density of the liquid.

It is possible to equip upright or horizontal reactors with one or more single orifice mixing nozzles. The term "single orifice mixing nozzles" is to be understood to refer to nozzles in which, after converting the pressure drop between nozzle feed and oxidator pressure into velocity energy, the gas containing oxygen and the oxidator liquid are mixed and at the same time produce a strong turbulence of gas and liquid. Most of the substance conversion to the products takes place in this highly disperse phase formed within the nozzles and which enters at high velocity into the reactor liquid.

The single orifice mixing nozzles used in the invention are two-substance nozzles with "inner" (interior) mixing (cf. ULLMANN, Volume 2, page 256, FIG. 4, right). Such a nozzle has only one narrow exit orifice in which the gas/liquid-mixing point with the highest mass velocity lies.

The gas is fed into the inner mixing space parallel to the nozzle axis or preferably at an angle to the axis. A mixing pipe (diffusor) may be affixed onto the exit opening of the nozzle.

In contrast thereto are nozzles with separate, for example, concentric exit openings from the nozzle for each substance and "exterior" mixing of the substances in one long mixing zone outside of the nozzle.

Nozzles with "exterior" mixing are not usable according to the invention, because such nozzles allow gas to escape and results in small yields and the formation of side products during the reaction.

The kind and amount of catalyst used is the same as in the conventional process. In general, cobalt salts are used in amounts of 50 to 500 ppm of cobalt, plus preferably manganese salts in amounts of 5 to 50 ppm of manganese, referred to the weight of the reaction phase, preferably in the form of acetates, or generally as fatty acid ($C_2$ to $C_{18}$) salts.

The catalyst salts can be solved in the reaction phase or in said low fatty acids or other carboxylic acids.

The oxidation is performed discontinuously up to an established acid number and then the oxidator liquid is worked up. It has been found that by the invention the selectivity of the reaction with regard to the target products is considerably increased in comparison to the standard process in bubble column reactors at the same acid number, and hence at the same degree of oxidation. Accordingly the amount of by-products is lowered, which is apparent from the diminished amounts of $CO_2$ and oxygen produced during an oxidation charge, in comparison to the conventional manner of operation. Especially surprising is that several times more air can be put through and utilized per unit of volume and weight of oxidator liquid with a correspondingly increased yield per unit volume and time, i.e., a substantially smaller apparatus for an equal amount of production. Thus, in spite of a comparatively small oxidator capacity and several times the heat production compared with the conventional method, the temperature in the reaction zone can be better controlled, air breakthrough can be prevented, and also a higher selectivity of the product and a higher yield with respect to the starting substance is achieved.

Also subject matter of the invention is the apparatus for the practice of the method, consisting of a controlled-temperature, pressurized, upright or horizontal, discontinuously or continuously operated oxidator, with input of the starting substances, removal of the product as well as removal of gas, and a circulating of the oxidator liquid, the circuit consisting of a drain from the oxidator, a pumping system to increase the pressure, and one or more single orifice mixing nozzles disposed in the oxidator under the surface of the liquid and supplied with oxidation gas. Preferably the oxidator is provided with an input of evaporable liquid, preferably ahead of or into the single orifice mixing nozzles and/or a cooling system, preferably in the form of a heat exchanger, for reducing the temperature of the circulating liquid ahead of the single orifice mixing nozzles.

The various features of novelty which characterize the invention are pointed out with particularity in the claims annexed to and forming a part of this specification. For a better understanding of the invention, its operating advantages and specific objects obtained by its use, reference should be had to the accompanying drawing and descriptive matter in which there is illustrated and described a preferred embodiment of the invention.

DESCRIPTION OF A PREFERRED EMBODIMENT

Figure 1:
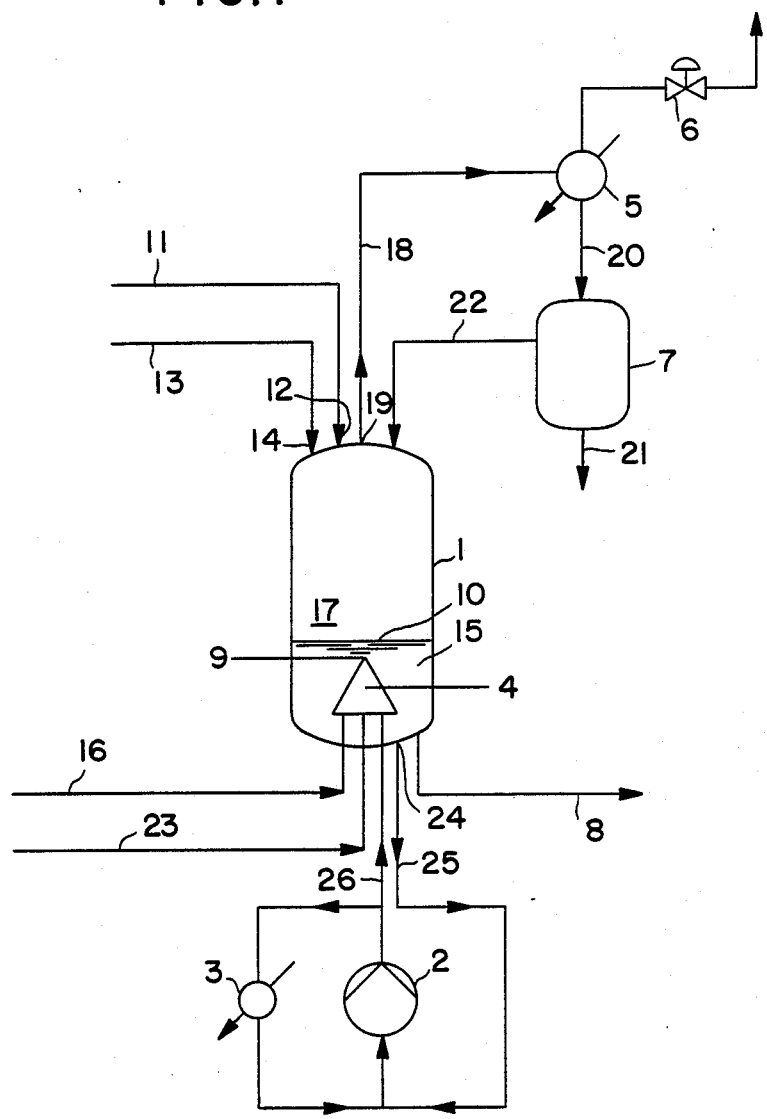
FIG. 1 diagrammatically represents an arrangement of apparatus for the invention.

Referring to FIG. 1, a reactor 1 is charged with a catalyst-containing solution 11 through a feed nozzle 12. The amount of catalyst contained in solution is such that the amount of catalyst in reactor 1, based on the total amount of reactants, will range from about 50 to about 500-600 ppm. Reactor 1 is also charged with PX (p-xylene) and a working ester 13 through a feed nozzle 14 to form a liquid reaction phase 15 in reactor 1. Reactor 1 is sometimes referred to as an oxidator. The reaction phase 15 is heated to a starting temperature in the range of from 110° to 200° C., and preferably to a temperature of from 130° to 170° C. Subsequently, oxygen or an oxygen-containing gas is introduced into reactor 1 through line 16. The oxygen-containing gas will actually enter the interior space 17 of reactor 1 through one or more of the single orifice mixing nozzle system 4. The reaction phase 15 is recirculated, as subsequently described, and is reinjected into reactor 1 through nozzle system 4 along with the oxygen-containing gas such that the reaction phase 15 is atomized with the admixture of the oxygen-containing gas in the nozzle or the nozzle system 4. The nozzle system 4 includes at least one nozzle as will be subsequently described.

In reactor 1, the reaction phase 15 is maintained in such a condition and amount such that the approximate upper surface 10 of the reaction phase 15 is maintained at a level of from about 0.3 to 0.5 meters above the opening or orifice of one or more of the single orifice mixing nozzle system 4 during the introduction of the oxygen-containing gas. A gas phase 18, substantially free of oxygen, is exhausted from reactor 1 through an exhaust outlet 19 and passes through a condensor 5 wherein the exhaust gas 18 is substantially freed from condensible components. The so-treated exhaust gas is carried away through an expansion valve 6 and an exhaust gas washer (not shown).

A condensate 20 from the condensor 5 passes into a phase separator 7 wherein the condensate is separated into an aqueous phase 21, to be worked up if desired, and an aromatic phase 22 which is fed into reactor 1. The reactor liquid with an established acid number is withdrawn from reactor 1 through line 8.

Under the surface 10 of the reaction phase 15 is the nozzle system 4 which consists of one or more nozzles provided with a mixing chamber and openings for supplying oxidation air and for feeding circulating liquid, i.e., oxidator liquid. From the orifices 9 of the nozzle(s) of nozzle system 4 a highly disperse reaction phase escapes from the nozzle (or the nozzles) into the oxidator liquid. If desired, the single orifice mixing nozzles can include structure for feeding inert liquids, supplied via line 23, to be evaporated as cooling liquid with the oxygen-containing gas and liquid.

The reactor 1 has a liquid outlet 24 whereby a portion of the oxidator liquid is withdrawn through line 25. The removed portion is circulated through a pump 2 whereby the liquid pressure is increased to a pressure greater than the pressure condition within reactor 1. The withdrawn liquid is cooled in a heat exchanger 3 and repumped by pump 2 through line 26 back into the nozzle system 4 whereby it is reinjected into the reactor in an atomized form with the oxygen-containing gas and optionally the inert liquid.

Figure 2A:
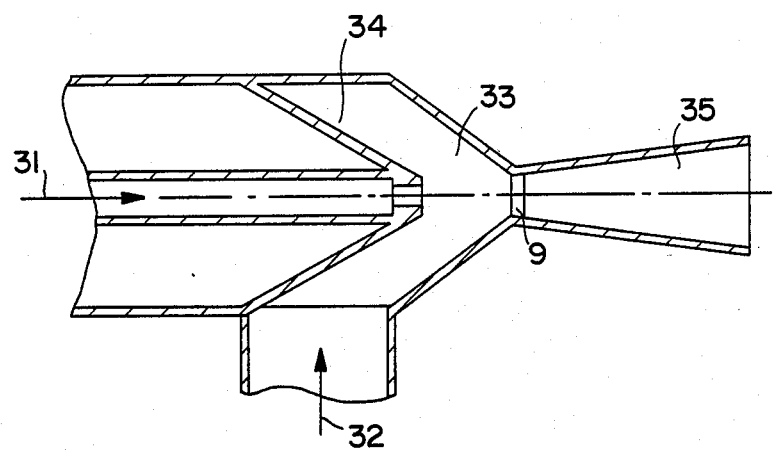
FIG. 2 shows embodiments of mixing nozzles useful in the invention.

In FIG. 2 are shown single orifice mixing nozzles useful in the invention. As shown in FIG. 2, gas 32 is introduced into a section of the nozzle and liquid, i.e., reaction phase (31) coming from the pump, is also introduced. The gas and liquid phases are subject to a mixing action in internal mixing space 33 so as to form a gas-liquid mixture. The gas-liquid mixture escapes through the single orifice 9 of the nozzle into the reaction phase inside of the reactor. In FIG. 2a, the gas 32 is introduced at an angle to the nozzle axis and is led by a cone 34 in direction to the orifice 9. A diffusor 35 may be affixed onto the nozzles exit orifice 9.

In the Examples, the mass velocity is 2900 kg/sec. m². The starting materials were preheated to 60° C. and heated to the starting temperature by pumping through the heat exchanger 3, which was heated at the beginning. During the reaction the heat exchanger is used as a cooling device due to the heat formed by the exothermic reaction.

EXAMPLE 1

In the Examples the nozzle of FIG. 2a is used, wherein air as oxygen-containing gas is introduced at an angle to the nozzle axis.

13.5 kg of p-xylene (99.3 wt.-%) and 31.5 kg of working ester containing 87 wt.-% of PTE with catalyst contents of 150 weight-parts per million of cobalt and 13 weight-parts per million of manganese in the form of acetate are placed into a reactor of 300 mm diameter, in an oxidation system according to that of the drawing. After reaching a starting temperature of 130° C., an average Vn=8.0 cu m per hour of air (Vn=standard volume at 0.1013 MPa pressure absolute at 0° C.) was introduced into the fluid-bed nozzle for a period of 4.1 hours at a reactor pressure of 0.8 MPa and a nozzle bias pressure of 1.2 MPa absolute. In the course of reaction the temperature was raised to 165° C. At an acid number of 197 the oxidation was stopped. Generally the acid number rises from about zero in the raw material to up to 300, preferably up to 250 in the oxidized reaction phase. The temperature was reduced in the circuit with the heat exchanger by 4° to 10° C. below the temperature in the oxidator. The total amount of air introduced amounted to Vn=32.7 cu.m. The continuously measured composition of the exhaust gas averaged 1.45 vol.-% $CO_2$, 1.6 vol.-% oxygen gas, and 1.15 vol.-% other, the balance being nitrogen and noble gases from the air. A selectivity of 94.1% was computed on this basis, i.e., 1.85% more than in the conventional process at the same acid number, which was confirmed by the amounts of target products that were produced. The yield per unit of volume and time, with respect to the reaction capacity, was around 180 to 320 cu.m. of air per hour per cubic meter in various similar throughputs. In conventional bubble column reactors this averages around 40 to 45 cu.m. of air per hour per cubic meter.

EXAMPLE 2

In the same manner as in Example 1, as regards catalyst, pressure and rate of reaction, the oxidation was repeated with a total amount of air input of Vn=33.8 cu.m. until an acid number of 189 was reached. The average exhaust gas composition was 1.38 vol.-% $CO_2$, 3.0 vol.-% oxygen gas, and 1.12 vol.-% other. The selectivity was 93.5%, i.e., 1.5% more than in the case of the same acid number in conventional bubble column reactors.

It will be understood that the specification and examples are illustrative but not limitative of the present invention and that other embodiments within the spirit and scope of the invention will suggest themselves to those skilled in the art.

We claim:

1. A method for preparing benzene carboxylic acids and benzene dicarboxylic acid esters and their mixtures comprising: introducing into an oxidator, xylene and/or toluylic acid ester and a heavy metal-containing oxidation catalyst to form a reaction phase; and oxidizing the xylene and/or toluylic acid ester with oxygen or an oxygen-containing gas in the presence of the heavy metal-containing oxidation catalyst at a temperature of 100° to 200° C. with the use of elevated pressure of 0.2 to 1.5 MPa, wherein said oxidizing is carried out by withdrawing at least a portion of the reaction phase and recycling the reaction phase into the reactor in the form of a highly dispersed reaction phase by atomizing the reaction phase with the addition of oxygen or an oxygen-containing gas in at least one single orifice mixing nozzle to bring about the oxidation.

2. The method of claim 1 wherein the recycled reaction phase is under pressure higher than the pressure in the oxidator.

3. The method of claim 1 wherein a volumetric ratio in the nozzle of the gas to the reaction phase under standard conditions is 1 to 20.

4. The method of claim 3 wherein the nozzle has an initial nozzle pressure and the difference between the initial nozzle pressure and the pressure in the oxidator amounts to 0.1 to 3.0 MPa.

5. The method of claim 1 further comprising reducing the temperature of the oxidator liquid by means of a heat exchanger before the liquid enters into the single orifice mixing nozzle.

6. The method of claim 1 wherein the oxidator liquid fed to the nozzle is mixed with an evaporating liquid that is inert at the reaction temperature.

7. The method of claim 1 further comprising establishing the oxidation temperature in the single orifice mixing nozzles corresponding to the heat produced in the reaction is accomplished by lowering the temperature in the circulating liquid before entry into the nozzles and/or by dosed feeding of evaporating inert liquids.

8. The method of claim 1 wherein a mass velocity of 1,500 to 6,000 kg/sec $m^2$ is maintained in the single orifice mixing nozzles at a point of mixing the reaction phase with the gas.

9. The method of claim 1 wherein the single orifice mixing nozzle is a gas/liquid mixing nozzle having an inner mixing space, through the orifice of the nozzle leaving a mixture of gas and reaction phase of the highest mass velocity into the oxidator.

10. The method of claim 1 wherein the temperature is 130° to 170°C.

11. The method of claim 1 wherein the elevated pressure is 0.5 to 0.9 MPa.

12. The method of claim 3 wherein the volumetric ratio is 3 to 8.

13. The method of claim 4 wherein the difference between the initial nozzle pressure and the pressure in the oxidator is 0.2 to 1.0 MPa.

14. The method of claim 8 wherein the mass velocity is 2,000 to 4,000 kg/sec $m^2$.

* * * * *

UNITED STATES PATENT AND TRADEMARK OFFICE
CERTIFICATE OF CORRECTION

PATENT NO. : 4,908,471
DATED : March 13, 1990
INVENTOR(S) : Hans Leuck et al

Figure 2B:
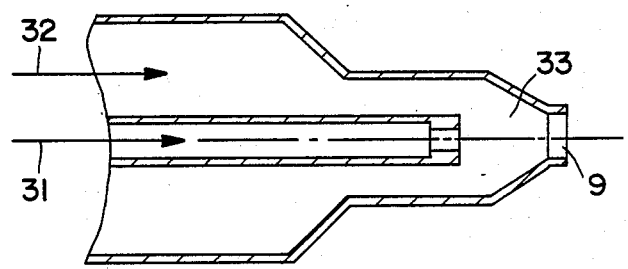

It is certified that error appears in the above-identified patent and that said Letters Patent is hereby corrected as shown below:

Column 5, lines 25-26,
    delete lines 25-26 entirely and insert
    --Figure 2a shows a mixing nozzle useful
    in the invention; and Figure 2b shows
    another mixing nozzle useful in
    the invention--.

Column 6, line 25, delete "2" and insert --2a and FIG. 2b--.

Column 6, line 26, delete "FIG. 2" and insert
    --each of FIGS. 2a and 2b--.

Signed and Sealed this

Sixth Day of April, 1993

*Attest:*

STEPHEN G. KUNIN

*Attesting Officer*     *Acting Commissioner of Patents and Trademarks*